United States Patent [19]

Muller et al.

[11] 4,448,881

[45] * May 15, 1984

[54] FERMENTABLE SUGAR FROM THE HYDROLYSIS OF STARCH DERIVED FROM DRY MILLED CEREAL GRAINS

[75] Inventors: Werner C. Muller, Dobbs Ferry, N.Y.; Franklyn D. Miller, Cincinnati, Ohio

[73] Assignee: National Distillers and Chemical Corporation, New York, N.Y.

[*] Notice: The portion of the term of this patent subsequent to Sep. 1, 1998 has been disclaimed.

[21] Appl. No.: 391,324

[22] Filed: Jun. 23, 1982

Related U.S. Application Data

[63] Continuation-in-part of Ser. No. 219,011, Dec. 22, 1980, abandoned, which is a continuation-in-part of Ser. No. 112,033, Jan. 14, 1980, Pat. No. 4,287,304.

[51] Int. Cl.$^3$ .......................... C12P 7/14; C12P 7/06
[52] U.S. Cl. ...................................... 435/162; 435/99; 435/161; 127/38; 127/69; 426/11; 426/48
[58] Field of Search .................. 435/96, 99, 161, 162, 435/48; 127/38, 68–70; 426/11

[56] References Cited

U.S. PATENT DOCUMENTS

| | | | |
|---|---|---|---|
| 2,698,826 | 1/1955 | Peltzer, Sr. | 435/161 |
| 3,236,740 | 2/1966 | Smith et al. | 435/161 |
| 3,251,717 | 5/1966 | Honeychurch et al. | 127/69 X |
| 4,069,103 | 1/1978 | Muller | 435/99 |
| 4,089,745 | 5/1978 | Antrim et al. | 435/99 |
| 4,181,748 | 1/1980 | Chwalek et al. | 127/68 X |
| 4,217,414 | 8/1980 | Walon | 435/99 X |

*Primary Examiner*—Lionel M. Shapiro
*Attorney, Agent, or Firm*—Kenneth D. Tremain

[57] ABSTRACT

Starch derived from a dry milled cereal grain such as corn or milo is hydrolyzed to provide a sterile aqueous fermentable sugar solution which is especially adapted for fermentative conversion to ethanol with minimum thermal expenditure. Following an initial mild hydrolysis to thin, or liquefy, the starch, substantially all of the water insoluble protein and oil components, and a portion of the water soluble components, e.g., sugars, lipids, proteins and vitamins, are separately recovered from the partial starch hydrolysate with the water solubles being recycled to the system. Thereafter, the partial starch hydrolysate is subjected to further hydrolysis to provide an aqueous solution of fermentable sugar.

17 Claims, 1 Drawing Figure

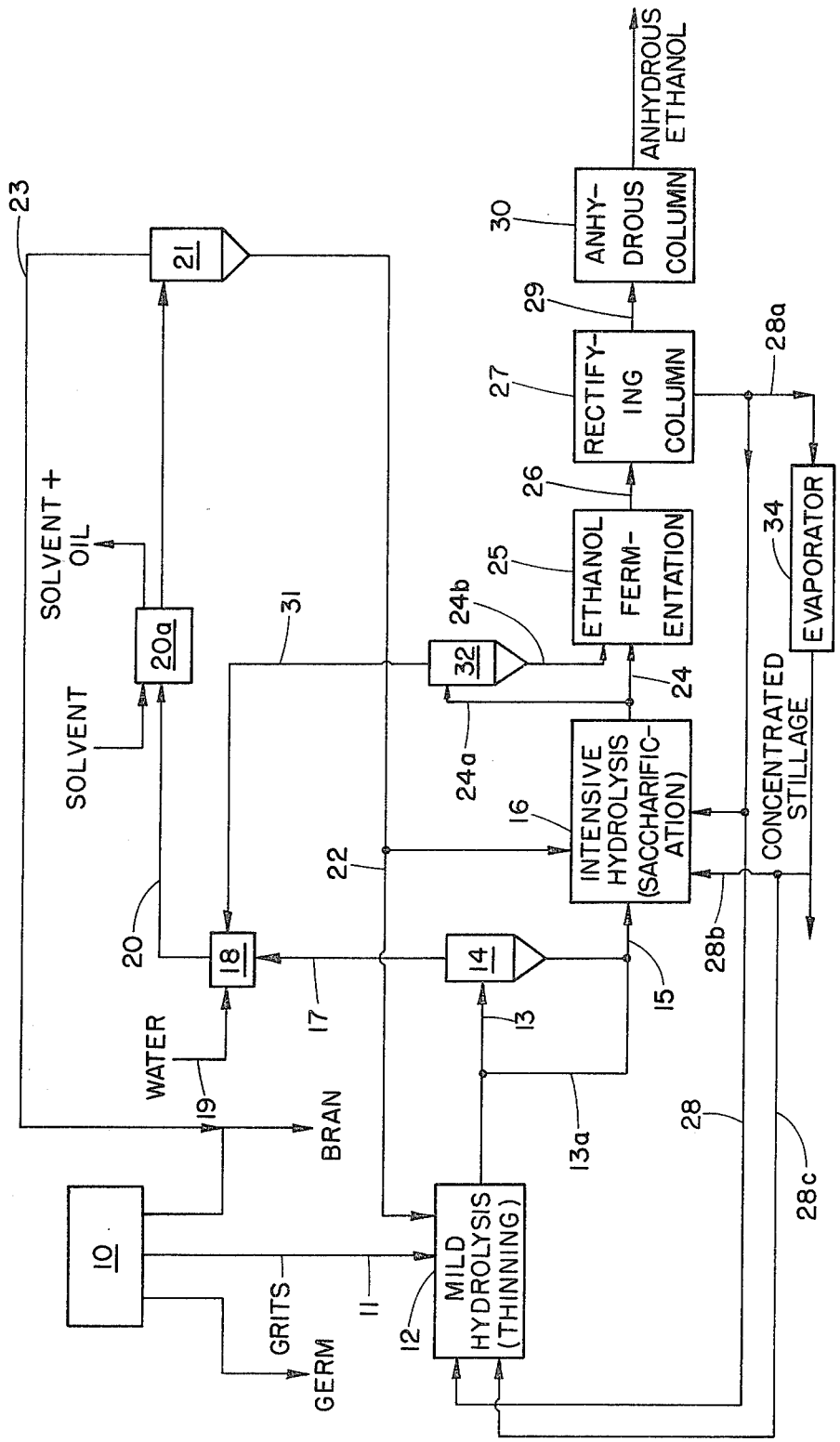

FERMENTABLE SUGAR FROM THE HYDROLYSIS OF STARCH DERIVED FROM DRY MILLED CEREAL GRAINS

CROSS REFERENCE TO RELATED APPLICATION

This application is a continuation-in-part of commonly assigned copending U.S. patent application Ser. No. 219,011 filed Dec. 22, 1980, now abandoned, which in turn, is a continuation-in-part of application Ser. No. 112,033, now U.S. Pat. No. 4,287,304.

BACKGROUND OF THE INVENTION

1. Field of the Invention

This invention relates to the acid and/or enzymatic hydrolysis of starch derived from dry milled cereal grains such as corn and milo to provide fermentable sugar.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefication and saccharification), the fermentation of sugar to a dilute solution of ethanol ("beer") and the recovery of anhydrous ethanol by distillation, have been modified in numerous ways to achieve improvements in product yield, production rates and so forth (see, for example, U.S. Pat. No. 3,236,740 and the booklet "Industrial Alcohol by Continuous Fermentation and Vacuum Distillation With Low Energy Consumption", of Chemapec, Inc., Woodbury, N.Y.). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum based raw materials. To data, however, relatively little concern has been given to the energy and raw material requirements for manufacturing ethanol from biomass and consequently, little effort has been made to minimize the thermal expenditure and waste incurred in carrying out any of the aforesaid discrete operations involved in the manufacture of ethanol from vegetative sources.

Processes for the enzymatic hydrolysis of starch to provide fermentable sugars are well known (viz., U.S. Pat. Nos. 2,219,668; 2,289,808; 2,356,218; 2,431,004; 2,676,905; 3,308,037; 3,337,414; 3,423,239; 3,425,909; 3,551,293; 3,565,764; 3,591,454; 3,592,734; 3,654,081; 3,720,583; 3,910,820; 3,912,590; 3,922,196; 3,922,197; 3,922,198; 3,922,199; 3,922,200; 3,922,201; 3,969,538; 3,988,204; 3,922,261; 3,966,107; 3,998,696; 4,014,743; 4,016,038; 4,017,363; 4,028,186; 4,032,403; and, C. Bos et al., "Experience with the DDS-Krøyer Direct Hydrolysis Process", *Die Starke,* Vol. 26, No. 6, 1974, pp. 181-184). Similarly, processes for the acid hydrolysis of starch to provide fermentable sugars are also well known (viz., U.S. Pat. Nos. 2,203,325; 2,210,659; 2,359,763; 2,393,095; 2,395,907; 2,565,404; 2,946,706; 2,954,304; 2,989,425; 3,169,083; 3,200,012; 3,236,687; 3,313,654; 3,446,664; 3,484,287; 3,607,395; and, 4,137,094). While these and similar processes are for the most part readily adaptable to the hydrolysis of the finely divided, relatively pure starch derived from conventional processes of wet milling cereal grains, their application to the starch-containing fractions obtained from processes of dry milling cereal grains as currently practiced would be uneconomically wasteful of the protein and edible oil associated with these fractions which in the case of corn and milo, is especially significant. Wet milling processes typically remove all but an insignificant amount of non-starch materials, i.e., protein, cellulosic fiber and oil, from the starch component of the grain, the non-starch materials finding valuable application in their own right as animal feeds and feed supplements. However, from the standpoint of producing starch for conversion to sugar, the sugar to dilute ethanol and the dilute ethanol to essentially anhydrous ethanol, conventional wet-milling processes are undesirable because of the need to ultimately remove the large amounts of process water involved.

Where, as in the case of low cost industrial ethanol, a minimal use of energy is necessary to achieve an economically viable process, a relatively energy and capital intensive process such as one based on wet-milled corn starch as the starting material can be disadvantageous. For this reason, the hydrolytic conversion of starch derived from any of the known and conventional dry milling processes is especially desirable in an industrial scale anhydrous ethanol program since these processes employ no added water beyond the moisture which is already naturally present in the grain. Thus, for example, in a typical dry corn milling process, the kernels are broken by impact and the resulting fractions made up of grits and fine feed which contain the bulk of the starch and significant quantities of oil, protein and cellulosic fiber, germ which contains most of the oil content of the kernels, and hulls which contain the major portion of the fiber, are separated employing degerminators, sifters, aspirators and gravity separators. A typical dry corn milling product analysis (pounds per bushel) is as follows:

| STREAM | ANALYSIS ON YELLOW CORN #2, LB/BUSHEL (DRY BASIS) | | | |
|---|---|---|---|---|
| | CORN | GERM | BRAN | GRITS |
| Starch | 34.27 | 1.33 | 1.14 | 31.80 |
| Protein | 4.28 | 0.64 | 0.27 | 3.37 |
| Oil | 2.05 | 1.05 | 0.17 | 0.83 |

-continued

| | ANALYSIS ON YELLOW CORN #2, LB/BUSHEL (DRY BASIS) | | | |
|---|---|---|---|---|
| STREAM | CORN | GERM | BRAN | GRITS |
| Fiber | 1.22 | 0.21 | 0.57 | 0.44 |
| Nitrogen-Free Extract | 5.00 | 1.32 | 1.50 | 2.18 |
| Ash | 0.77 | 0.21 | 0.15 | 0.41 |
| Dry Solids | 47.59 | 4.76 | 3.80 | 39.03 |
| Moisture | 8.41 | 0.84 | 0.68 | 6.89 |
| TOTAL | 56.00 | 5.60 | 4.48 | 45.92 |

As this analysis indicates, the grits contain 92.8% of the starch, 78.7% of the protein and 40.5% of the oil of the whole corn kernels. Direct complete hydrolysis of the grits would therefore make these substantial amounts of protein and oil unavailable for use as comestibles.

Accordingly, there has heretofore existed a need for a process for converting starch derived from dry milled cereal grains to fermentable sugars while recovering substantially all of the protein and oil content of the starch component of the dry milled grain prior to the complete hydrolysis of the starch. The term "cereal grain" as used herein is to be understood in its commonly used sense and is inclusive of all varieties of corn (maize), milo, wheat, rice, and the like.

SUMMARY OF THE INVENTION

In accordance with the present invention, a process is provided for converting starch derived from dry milled whole grain, which starch contains varying amounts of water insoluble protein and oil depending upon the nature of the grain, and which are relatively substantial in the case of corn and milo, and relatively small amounts of one or more water soluble components selected from the group consisting of sugar, protein, vitamin and mineral, to fermentable sugar to provide substrate for the thermally efficient large-scale production of ethanol. An aqueous slurry of the starch is subjected to thinning, or liquefying, hydrolysis via enzyme or acid catalyst hydrolysis to provide a sterile partial starch hydrolysate. This hydrolysate contains a phase made up of water insoluble protein and oil and a water soluble phase made up of the water soluble components of the starch. The proteins originally present in the starch undergo modification as a result of the thinning hydrolysis thereby facilitating their separation and recovery by centrifugation. The slurry is then optionally separated into an aqueous partial starch hydrolysate portion containing a part of the water soluble components and a water insoluble protein and oil portion containing the remaining part of the water soluble components. The aqueous partial starch hydrolysate portion is subjected to further intense hydrolysis, preferably to the point of 80–93% conversion to glucose, and, optionally, clarified before the resulting aqueous solution of fermentable sugar together with most of the water soluble component of the original starch feed is conveyed to a fermentation unit where conversion of the sugar to ethanol and further hydrolysis of any remaining partial starch hydrolysate to fermentable sugar takes place (when saccharifying enzyme is present).

The previously separated water insoluble protein and oil portion may be combined with water to dissolve the water soluble components associated therewith with the resulting aqueous slurry thereafter being separated into a protein and oil portion substantially free of any of the water soluble components of the original starch and starch hydrolysate, and an aqueous portion containing water soluble components. The protein and oil may be used directly in animal feed or, if desired, they may be separately recovered for individual use. The aqueous portion containing water soluble components of the starch is advantageously recycled for use in the first or second hydrolysis step.

Employing the foregoing starch hydrolysis process, only minimal quantities of fresh water need be used to accomplish conversion of the starch to fermentable sugar thus reducing the amount of water which must be removed from product ethanol obtained from the fermentation of the sugar, and consequently, the amount of thermal energy which must be expended in the manufacture of the ethanol. Moreover, substantially all of the water insoluble protein contained in the original starch can be recovered for other commercially valuable uses, notably animal feed, and due to the water recycle feature which is made possible by the process herein, a good portion of the water soluble components of the starch are retained in the solution of product fermentable sugar and are therefore available for satisfying certain nutrient requirements of the yeast employed in the fermentation of the sugar to ethanol.

The process herein with appropriate modification is also applicable to the hydrolysis of starch contained in degerminated cereal grains, i.e., grains from which a portion of the oil has been removed, dehulled grains, and degerminated and dehulled grains.

The term "fermentable sugar" as used herein is to be understood as referring to a single fermentable sugar such as glucose (dextrose), fructose, maltose, or sucrose but more commonly will be applicable to these and similar fermentable sugars and sugar oligomers in admixture.

BRIEF DESCRIPTION OF THE DRAWING

The accompanying drawing is a diagrammatic flow sheet illustrative of the starch hydrolysis process of the present invention as applied to corn. The process contemplates the use of known and conventional equipment which is readily available from several suppliers.

DESCRIPTION OF THE PREFERRED EMBODIMENTS

Referring to the drawing, the conventional dry milling of corn carried out in unit 10 results in three fractions, the germ which contains most of the oil content of the corn kernels, the grits (combined with the fine feed) which contains most of the starch but also substantial amounts of water insoluble protein and oil and significant quantities of water soluble components as indicated above, and the bran or hulls, which contains the bulk of the fiber (cellulose) of the corn. While the process of this invention can be carried out upon the whole dried milled corn, i.e., corn containing substantially all of the oil content of the product, in the embodiment shown, hydrolysis is carried out upon corn grits, i.e., corn containing only a portion of the oil content of whole corn kernels. The starch fraction of the degerminated dry milled corn is conveyed through 11 to a hydrolysis unit 12 where the starch molecules are initially depolymerized to form partial hydrolysates. This first hydrolysis, i.e., thinning or liquefying, can be effected in a known manner in the presence of a liquefying enzyme or a strong acid such as hydrochloric acid, sulphuric acid, phosphoric acid, nitric acid, etc. The operating conditions for the enzyme and acid hydrolysis of starch are well known and do not in themselves constitute a part of this invention. In general, an initial acid hydrolysis is carried out with a sufficient amount of strong acid to provide a pH of from about 1.0 to about 2.5, this mild hydrolysis of the starch being carried out at a temperature of from about 350° F. to 500° F. and preferably at a temperature of from about 375° F. to about 450° F. These temperatures are conveniently obtained by injecting steam into the hydrolysis unit. Pressures must be substantially above the saturation pressure equivalent to the operating temperature. Pressures on the order of from about 5 to about 250 psig, and advantageously, from about 5 to about 150 psig, can be used depending on saturation pressure. Residence time of the starch slurry in mild hydrolysis unit 12 to effect partial hydrolysis and sterilization of the starch is not a critical consideration. In general, residence times of up to about 15 minutes, and preferably of up to about 5 minutes, provide good results. Typically, the preliminary acid hydrolysis herein is conducted for a period of time which will yield a slurry containing from about 12 to about 24 dextrose equivalent (D.E.), and preferably from about 16 to about 20 D.E. Under the foregoing conditions of hydrolysis, the accompanying water insoluble protein will undergo modification permitting their ready recovery by such conventional means as centrifugation. The partially hydrolyzed starch stream is optionally conveyed in whole or in part through line 13 to a first centrifuge, filter or other separating device 14 where an aqueous partially hydrolyzed starch stream containing a portion of solubles is recovered as underflow through line 15 to undergo a second, or final, intensive hydrolysis to fermentable sugar in starch hydrolysis unit 16 and the stream of protein and oil containing the remaining portion of solubles is recovered as overflow through line 17 to be washed with fresh water entering unit 18 through line 19 and possibly combined with a second overflow stream from separator 32 via line 31. In order to facilitate rapid conversion of the starch a portion of the partially hydrolyzed starch stream can optionally be conveyed in whole or in part through line 13a directly to starch hydrolysis unit 16. This second hydrolysis can be accomplished with strong acid or a saccharifying enzyme.

The washed aqueous stream of protein and oil is conveyed through line 20, advantageously to an oil separating unit 20a, wherein the oil is removed in a known or conventional manner such as settling or extracting with a solvent, e.g., n-hexane, and the de-oiled protein stream is then passed to a second centrifuge, filter or other separating device 21 with the aqueous solubles-containing underflow being transferred through line 22 to satisfy part or all of the process water requirements of mild hydrolysis unit 12 or intensive hydrolysis unit 16 in a subsequent starch conversion sequence. The protein overflow, largely devoid of water soluble components, is recovered from centrifuge 21 through line 23 where it can be combined with the bran fraction of the dry milled corn to provide a nutritious animal feed or feed supplement. Alternatively, the total wash stream 20 can be directly separated in 21 with the oil being used as a nutrient for animal feed. The further hydrolysis of the aqueous stream of partial starch hydrolysates in starch hydrolysis unit 16 also can be carried out with acid or enzyme.

If acid is contemplated, it is advantageous to effect the second hydrolysis in accordance with the process disclosed in commonly assigned copending U.S. patent application Ser. No. 91,640, filed Nov. 5, 1979, now abandoned in favor of continuation-in-part application Ser. No. 237,038, filed Feb. 23, 1981. In this process, an acidified partially hydrolyzed starch stream is combined with relatively high pressure steam to provide either a single phase or dual phase flow through a tubular reaction zone where rapid hydrolysis of the partial hydrolysate to a level of at least about 60 weight percent, and preferably at least about 80 weight percent, of the solids content to fermentable sugar takes place. To prevent any further reaction which might result in production of unfermentable sugar, reversion or degradation products, the hydrolysis is abruptly ended by suddenly relieving the pressure from the hydrolysis medium. In a single phase (liquid) flow operation, the partially hydrolyzed starch slurry at a pressure which is essentially the same as that employed in the first hydrolysis step is combined with an amount of steam sufficient to heat the slurry in this zone to a temperature of from about 275° F. to about 400° F. and preferably, from about 300° F. to about 375° F. In a dual phase (liquid and steam) flow operation, the acidified partial starch hydrolysate slurry is combined with an amount of steam sufficient to provide a temperature of from about 285° F. to about 420° F. or higher at saturation pressure. If enzyme is contemplated, it is advantageous to carry out further hydrolysis in accordance with the process disclosed in commonly assigned copending U.S. patent application Ser. No. 043,191, filed May 29, 1979, now abandoned in favor of continuation-in-part application Ser. No. 178,335 filed Aug. 15, 1980. In this process, the partially hydrolyzed starch slurry is combined with a saccharifying enzyme such as amyloglucosidase, advantageously together with a saccharification catalyst, under conditions of pH and temperature which promote maximum enzyme activity, e.g., a pH of from about 4.0 to about 5.0 and preferably from about 4.3 to about 4.7, and a temperature of from about 140° F. to about 145° F. Saccharification can proceed until such time as about 80 to about 93 weight percent of the solids content is obtained as fermentable sugar (2 to about 10 hours) with further saccharification being carried out in the fermentation unit.

Following further rapid hydrolysis, such as that described above, of the partial starch hydrolysates to fermentable sugar in 16, the stream may be optionally conveyed in whole or in part through line 24a to a clarifying device such as a separator 32, or the stream may be passed in whole or in part through line 24 to fermentation unit 25 with the dilute aqueous ethanol ("beer") resulting therefrom being sent through line 26 for concentration to about 90 volume percent, or higher, ethanol in rectifying column 27. Separator 32 clarifies the hydrolyzed stream, which is directed to fermentator 25 via line 24b, from a protein and oil containing overflow stream, which is passed through line 31 to unit 18.

The aqueous still bottoms from the rectifying column contain some proteins and other nutrients and are preferably recycled through line 28 to mild hydrolysis unit 12 or intense hydrolysis unit 16 to satisfy part of the water requirements of the starch conversion process herein. Optionally, the still bottoms may be routed through line 28a to evaporator 34 before being recycled via lines 28b and/or 28c for further hydrolysis. While such recycle minimizes the use of water in the overall production sequence from starch to anhydrous ethanol, it has the added advantage of retaining nutrients in the system, which can be utilized by yeast used in the fermentation of the sugar to ethanol. Moreover, hydrolyzable and fermentable carbohydrates normally discarded are retained in the system thus increasing the overall alcohol yield and process efficiency. Alternatively, the still bottoms in line 28 can be subjected to a drying operation with the residue therefrom being employed as an animal feed or feed supplement. The concentrated ethanol is conveyed through line 29 to anhydrous column 30 wherein azeotropic distillation to provide substantially water-free ethanol is carried out.

A typical material balance for the foregoing process carried out per bushel of corn is as follows:

| Stream | Whole Corn Kernels to Dry Milling Unit 10 | Bran Discharged From Dry Milling Unit 10 | Germ Discharged From Dry Milling Unit 10 | Oil Separated From Germ | Cake Remaining After Separation of 0.1 from Germ |
|---|---|---|---|---|---|
| Starch | 34.27 | 1.14 | 1.33 | — | 1.33 |
| Protein | 4.28 | 0.27 | 0.64 | — | 0.64 |
| Oil | 2.05 | 0.17 | 1.05 | 0.84 | 0.26 |
| Fiber | 1.22 | 0.57 | 0.21 | — | 0.21 |
| Ash | 0.77 | 0.15 | 0.21 | — | 0.21 |
| Nitrogen-Free Extract | 5.00 | 1.50 | 1.32 | — | 1.32 |
| Sugar | — | — | — | — | — |
| Insoluble Solids | — | — | — | — | — |
| Soluble Solids | — | — | — | — | — |
| Dry Solids | 47.59 | 3.80 | 4.76 | — | 3.92 |
| Water | 8.41 | 0.68 | 0.84 | — | 0.84 |
| Total | 56.00 | 4.48 | 5.60 | 0.84 | 4.76 |

| Stream | Grits in Line 11 | Partial Hydrolysate in Line 13 | Still Bottoms in Line 28 | Protein, Fiber and Oil in Line 17 | Supernatant Final Hydrolysate in Line 15 | Final Hydrolysate in Line 24 |
|---|---|---|---|---|---|---|
| Starch | 31.80 | — | — | — | — | — |
| Protein | 3.37 | 3.31 | — | — | — | — |
| Oil | 0.83 | 0.83 | — | — | — | — |
| Fiber | 0.44 | 0.44 | — | — | — | — |
| Ash | 0.41 | 0.41 | 0.74 | — | — | — |
| Nitrogen-Free Extract | 2.18 | 2.18 | — | — | — | — |
| Sugar | — | 35.33 | 1.90 | 1.95 | 35.28 | 37.23 |
| Insoluble Solids | — | — | — | 4.54 | — | 4.54 |
| Soluble Solids | — | — | — | 0.17 | 3.16 | 3.33 |
| Dry Solids | 39.03 | 42.56 | — | 6.65 | 38.44 | 45.10 |
| Water | 6.89 | 3.36 | 39.20 | 2.41 | 43.55 | 45.96 |
| Total | 45.92 | 45.92 | — | 9.06 | 81.99 | 91.06 |

What is claimed is:

1. A process for converting the starch fraction derived from whole dry milled cereal grain to a sterile aqueous solution of fermentable sugar, said starch containing water insoluble protein and oil and one or more water soluble components selected from the group consisting of sugar, lipid, protein, vitamin and mineral, which comprises:
   a. liquefying an aqueous slurry of the starch by hydrolysis to provide sterile aqueous partial starch hydrolysate slurry containing the water insoluble protein and oil and the water soluble components in substantially unaltered condition;
   b. separating the slurry resulting from liquefying step (a) into an aqueous sterile slurry of partial starch hydrolysate containing a part of the water soluble components and an aqueous slurry of water insoluble protein and oil containing the remaining part of the water soluble components; and
   c. intensively saccharifying the relatively thin aqueous slurry of partial starch hydrolysate to provide a sterile aqueous solution of fermentable sugar.

2. The process of claim 1 wherein said intensive saccharification of step (c) is continued until from about 80 to about 93 percent of said partial starch hydrolysate in converted to fermentable sugar.

3. The process of claim 1 wherein the cereal grain feed for liquefying step (a) is corn or milo.

4. The process of claim 1 wherein the cereal grain feed for liquefying step (a) is dehulled corn or milo.

5. The process of claim 1 wherein the sterile aqueous solution of fermentable sugar is subjected to fermentation to provide dilute aqueous ethanol.

6. The process of claim 5 wherein the dilute aqueous ethanol is concentrated in a rectifying column with the aqueous bottoms from said rectifying column being recycled for use in a subsequent liquefying step (a).

7. The process of claim 6 wherein the concentrated ethanol is substantially dehydrated to provide anhydrous ethanol.

8. The process of claim 1 further comprising the steps of:
   d. optionally conveying the partially hydrolyzed starch stream resulting from step (a) in whole or in part directly to said intensive saccharifying step (c);
   e. optionally clarifying the stream resulting from step (c) in whole or in part to provide a hydrolyzed starch stream for fermentation and a water insoluble protein and oil stream;

f. diluting the aqueous slurry of water insoluble protein and oil streams resulting from step (b) and (c) with water;

g. separating water from the water insoluble protein and oil resulting from step (f); and h. recycling the water recovered in step (g) for use in a subsequent liquefying step (a).

9. The process of claim 1 wherein liquefying step (a) is carried out with acid.

10. The process of claim 1 wherein saccharifying step (c) is carried out with acid.

11. The process of claim 1 wherein saccharifying step (c) is carried out with enzyme.

12. A process for converting the starch fraction derived from dry milled degerminated cereal grain to a sterile aqueous solution of fermentable sugar, said starch containing water insoluble protein, a relatively minor amount of the oil of the whole cereal grain, and one or more water soluble components selected from the group consisting of sugar, lipid, protein, vitamin and mineral, which comprises:

a. liquefying an aqueous slurry of the starch by hydrolysis to provide sterile aqueous partial starch hydrolysate slurry containing the water insoluble protein and the water soluble components in substantially unaltered condition;

b. separating the slurry resulting from liquefying step (a) into an aqueous sterile slurry of partial starch hydrolysate containing a part of the water soluble components and an aqueous slurry of water insoluble protein containing the remaining part of the water soluble components;

c. intensively saccharifying the aqueous slurry of partial starch hydrolysate to provide a sterile aqueous solution of fermentable sugar;

d. conveying a portion of the partially hydrolyzed starch resulting from step (a) directly to said intensive saccharrifying step (c);

e. clarifying the stream resulting from step (c) to provide a hydrolyzed starch stream for fermentation and a water insoluble protein stream;

f. diluting the aqueous slurry of water insoluble protein streams from step (b) and (c) with water;

g. separating water from the water insoluble protein resulting from step (f); and h. recycling the water recovered in step (g) for use in a subsequent liquefying step (a).

13. The process of claim 10 wherein said intensive saccharification of step (c) is continued until from about 80 to about 93 percent of said partial starch hydrolysate is converted to fermentable sugar.

14. The process of claim 12 wherein the cereal grain feed for liquefying step (a) is degerminated corn or milo.

15. The process of claim 12 wherein the cereal grain feed for liquefying step (a) is degerminated, dehulled corn or milo.

16. The process of claim 12 wherein the relatively minor amount of oil in the water insoluble protein fraction is removed therefrom.

17. The process of claim 12 wherein the intense saccharifying hydrolysis is carried out with enzyme.

* * * * *